United States Patent [19]
Murad

[11] Patent Number: 6,104,778
[45] Date of Patent: *Aug. 15, 2000

[54] X-RAY TREATMENT METHOD AND APPARATUS

[75] Inventor: Simon William Murad, West Chiltington, United Kingdom

[73] Assignee: Varian Systems, Inc., Palo Alto, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/951,652

[22] Filed: Oct. 16, 1997

[51] Int. Cl.$^7$ ........................................................ A61N 5/10
[52] U.S. Cl. .............................................. 378/65; 378/206
[58] Field of Search ........................................ 378/65, 206

[56] References Cited

U.S. PATENT DOCUMENTS 5,080,100   1/1992   Trotel ........................................ 378/65

FOREIGN PATENT DOCUMENTS

| 2 269 745 | 11/1975 | France . |
| 2 551 664 | 3/1985 | France . |
| 42 23 488 | 1/1994 | Germany . |
| 196 14 643 | 10/1997 | Germany . |
| WO 85/03212 | 8/1985 | WIPO . |

*Primary Examiner*—Craig E. Church
*Attorney, Agent, or Firm*—Workman, Nydegger & Seeley

[57] ABSTRACT

After a target region for an x-ray treatment is determined by a preliminary examination, a line which indicates the position and shape of this target region is marked on the patient's body by projecting a laser beam on such a line. This is accomplished by means of a laser light source and an optical system with two mirrors which are rotatable around mutually transverse axes of rotation. Thus, the region-indicating line can be made visible without causing the brightness of the environment to be reduced.

9 Claims, 2 Drawing Sheets

X-RAY TREATMENT METHOD AND APPARATUS

BACKGROUND OF THE INVENTION

This invention relates to a method in radio-therapy using an x-ray beam for treatment and an apparatus for using the method. More particularly, this invention relates to the technology of collimating, or "shaping," an x-ray beam for accurately delivering radiation to a preliminarily determined target region.

In radiotherapy such as in x-ray oncology, it is essential to deliver a precise amount of radiation, or dose, to a precisely defined region of a patient's body. Before a high-energy treatment machine is used to actually deliver the required radiation for treatment, therefore, it has been known to use a low-energy simulation machine preliminarily to determine exactly where the dose should be delivered and how it can be achieved.

After the target region has thus been determined but before the patient is actually treated by the high-energy machine, however, a scheme must be established on the basis of the data obtained on the target region whereby the high-energy radiation provided by the high-energy machine for the treatment can be properly collimated, or shaped, such that the dose will be received exactly in the target region determined preliminarily as described above. There are different ways to collimate, or shape, an x-ray beam, but practically all rely on the simple method of selectively blocking the beam by placing obstructions strategically in the radiation path. Since x-ray radiation is not visible, it has been known to place a visible light source at a position which is equivalent to the position of the x-ray source, to expose the patient to the visible light and to mark the region of interest.

Current collimator technology, as described above, is crude in that it allows depiction of the field by casting shadows, requiring wires, blocks and a so-called multi-leaf collimator to obstruct light.

A liquid crystal display device of a light transmitting type may be used to project an image drawn on the display device can be projected on the patient's body for marking the target region, but resolution of the image is limited by the pixel size and is generally poor and either a high-intensity light source must be used or the process must be carried out in a darkened room so that the image projected on the patient's body can be clearly observed.

SUMMARY OF THE INVENTION

It is therefore an object of this invention to provide an improved x-ray treatment method whereby a target region to be treated can be clearly marked such that the x-ray beam to be used for treatment can be effectively collimated, or shaped.

It is another object of this invention to provide such a method whereby the marking line for indicating the target region is clearly visible even without reducing the brightness of the environment.

It is another object of this invention to provide an apparatus for using such a method.

A method and apparatus embodying this invention, with which the above and other objects can be accomplished, may be characterized wherein, after a target region to be treated is determined by a preliminary examination, a line which indicates the position and shape of this target region is marked on the patient's body by projecting a laser beam along such a line. This is accomplished by means of a laser light source and an optical system with two mirrors which are rotatable around mutually transverse axes of rotation. Thus, the region-indicating line, as well as other symbols or reference lines, can be made visible without reducing the brightness of the environment.

BRIEF DESCRIPTION OF THE DRAWINGS

The accompanying drawings, which are incorporated in and form a part of this specification, illustrate an embodiment of the invention and, together with the description, serve to explain the principles of the invention. In the drawings.

DETAILED DESCRIPTION OF THE INVENTION

Figure 1:
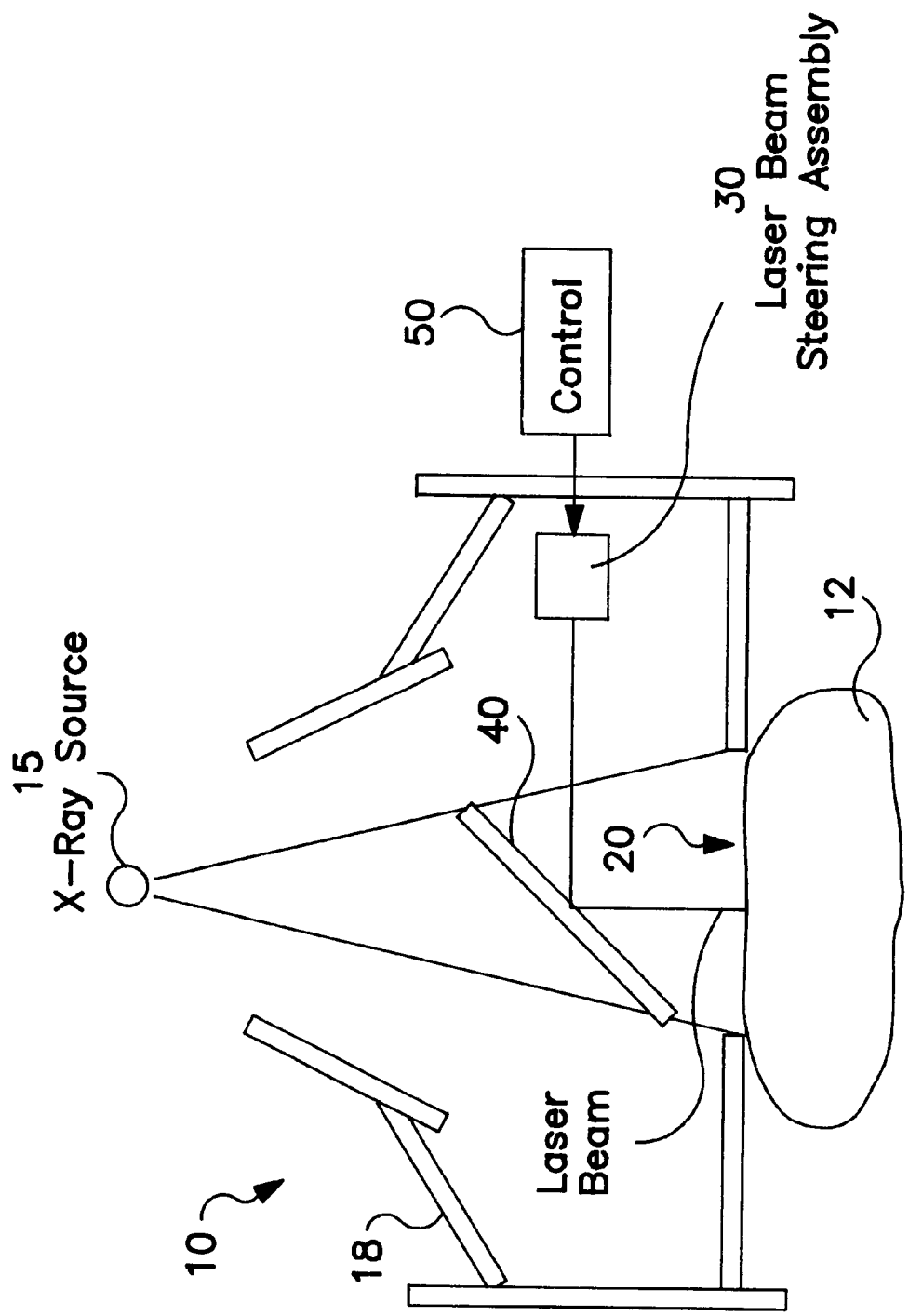
FIG. 1 is a block diagram, in part shown schematically by a sectional view, of an apparatus embodying this invention.

FIG. 1 shows schematically an apparatus 10 embodying this invention which may be used firstly to determine a region in a patient's body 12 where a specified doze of radiation is later to be delivered by another apparatus for treatment of the patient. A weak beam of x-ray (or "diagnostic x-ray beam")emitted from a source 15 is made incident on the patient's body 12 protected by a shield structure 18 with an aperture 20. The portion of the x-ray which passes through the aperture 20 and penetrates the patient's body 12 is received by a data collecting means (not shown) such as an x-ray sensitive photographic film. By analyzing the data thus collected, a target region to be treated can be determined. The data which serve to determine the region may be in the form of a set of images or digital data.

After the target region is thus determined, means for collimating, or shaping, the x-ray beam which is to be used for the actual treatment of the target region must be prepared. For this purpose, the apparatus serves, according to this invention, to mark the target region by making a beam of green laser light incident on the periphery of the target region such that a user can visually mark it clearly without dimming the room light or otherwise reducing the brightness of the environment.

Figure 2:
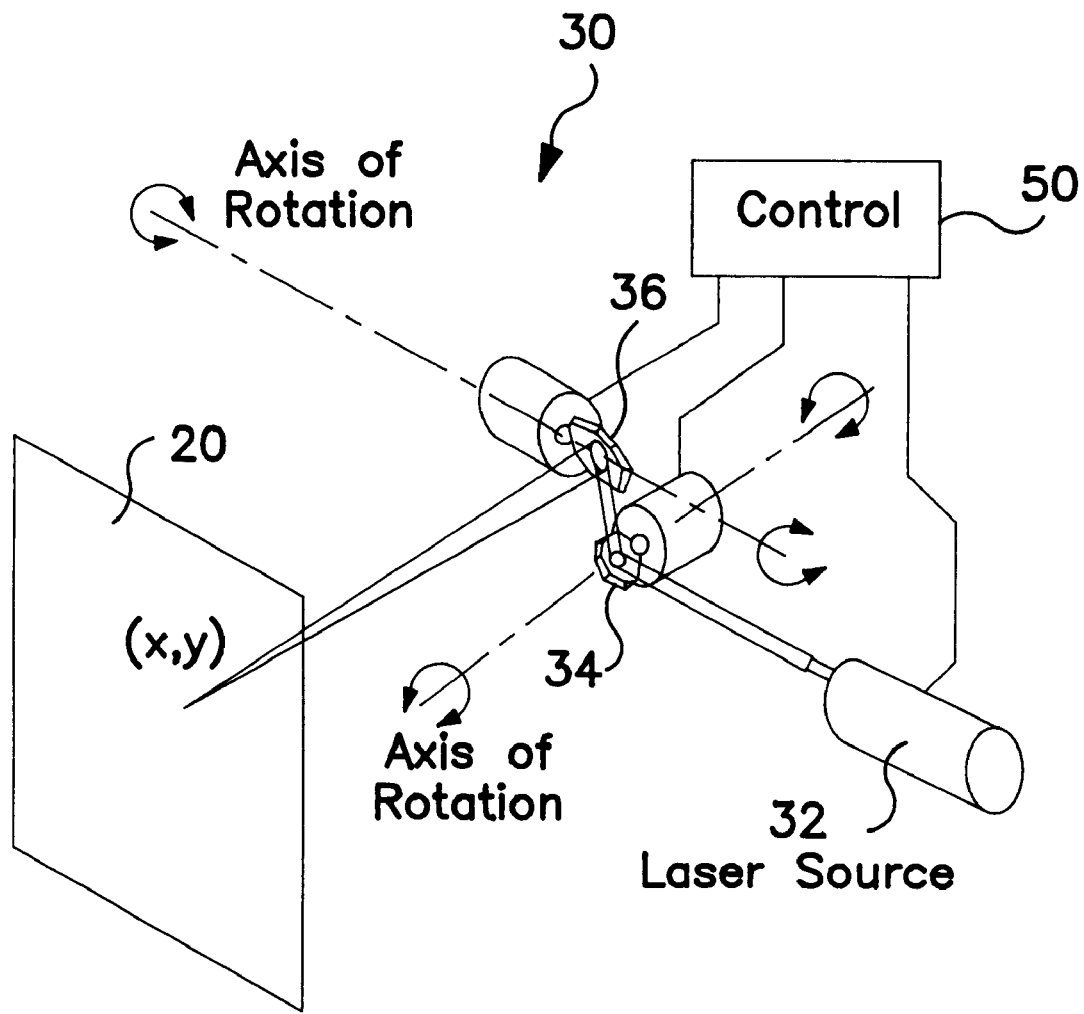
FIG. 2 is a schematic diagram of the optical system for the laser beam steering assembly.

For this purpose, the apparatus 10 is provided with a laser beam steering assembly 30, a transparent mirror 40 and a control unit 50. As schematically shown in FIG. 2, the laser beam steering assembly 30 includes a laser light source 32 for emitting a beam of laser light such as green light. Green light is preferred because it is easily visible when projected on the patient body surface, but this is not intended to limit the scope of the invention. Laser light of other colors may be substituted, depending on the circumstances.

The laser beam steering assembly 30 also includes two rotatable mirrors (referred to as the first mirror 34 and the second mirror 36). Each of the mirrors 34 and 36 is rotatable around an axis within a limited angular range. The axes of rotation of these mirrors 34 and 36 are transverse to each other, and the mirrors 34 and 36 and their axes of rotation are so positioned that the laser light beam emitted from its source 32 will be reflected by the first mirror 34 to be made incident on the second mirror 36 and reflected thereby to pass through the aperture 20 and to be made incident on the patient's body 12. The mirrors 34 and 36 can be individually rotated such that the laser light beam emitted from the source 32 can be caused to pass through any point on the area of the aperture 20 by successively reflected by the first mirror 34 and the second mirror 36.

The control unit 50 serves to control the angular positions, from one moment to the next, of the rotatable mirrors 34 and 36, or their rotary motions. After the user learns where is the target region to be treated, a closed line may be defined surrounding it, or otherwise indicating its position and shape. Other reference symbols, such as position-indicating crosses and scaled lines, which may be helpful if projected on the patient's body in designing a collimating device to be used with the high-energy treatment apparatus may be additionally included as figures to be marked. A program for moving the mirrors 34 and 36 is produced such that the laser beam from the source 32 can be successively directed to different points on the defined line and the additionally included symbols. If this scanning operation according to the program is carried out at a sufficiently high frequency, the user's eyes will see a stationary image, rather than an image of a moving point, on the patient's body.

It is to be noted at this moment that the lines and symbols are marked, according to this invention, by a laser beam made incident on the patient's body. Since the laser beam undergoes only reflections before reaching the patient's body without going through the likes of a liquid crystal, its intensity is not significantly attenuated. Thus, the image of the line indicating the position and shape of the target area and other additional symbols for convenience is clearly visible without dimming the light or otherwise reducing the brightness of the environment.

Although the invention has been described above with reference to a single situation, this is not intended to limit the scope of the invention. Many modifications and variations are possible within the scope of this invention. For example, although FIG. 1 showed an apparatus which can be used both for scanning a patient to determine the position and shape of a target region and for designing a collimator-simulator for designing a beam-shielding equipment, two separate apparatus may be used for these two operations. In addition to the laser light source and the laser beam steering assembly, a prior art optical system with an ordinary light source and movable field wires for casting shadow images, although they can be seen clearly only if the brightness of the environment is sufficiently reduced, may be incorporated. All such modifications and variations that may be apparent to a person skilled in the art are intended to be included within the scope of the invention.

What is claimed is:

1. An apparatus for visually marking an area on a patient for treatment by an x-ray signal, the apparatus comprising:

a light source that is capable of selectively emitting a beam of visible light;

an optical system capable of directing said beam of visible light to predetermined points on the patient;

a control unit operably connected to cause the optical system to direct the beam of visible light in a manner so as to create a visual indicator on the patient, wherein the visual indicator appears as a stationary image; and an x-ray source capable of emitting an x-ray signal to a target region on the patient, wherein the x-ray signal is shaped so as to be limited to the area defined by the stationary image.

2. The apparatus of claim 1, wherein the visible light is comprised of a laser light signal.

3. The apparatus of claim 1, wherein the optical system is comprised of a first mirror and a second mirror that are each operably connected to the control unit so as to direct the beam of visible light in a manner and thereby create the visual indicator on the patient.

4. The apparatus of claim 1, wherein the visual indicator is comprised of a illuminated line that appears to be visually disposed substantially about the periphery of the target region that is to be treated with the x-ray signal.

5. An x-ray treatment method comprising the steps of:

determining a target region on a patient for treatment by a therapeutic x-ray signal;

projecting a beam of visible light onto the patient so as to provide a visual indicator that designates the location of the target region on the patient's body;

generating the therapeutic x-ray -signal; and shaping the therapeutic x-ray signal in accordance with the position and shape of the visual indicator on the patient's body so that only the target region is exposed to the therapeutic x-ray signal.

6. The method of claim 5, wherein the visual indicator appears as a substantially stationary image.

7. The method of claim 5, wherein the visual indicator appears as a substantially stationary image of a line disposed about the periphery of the target region on the patient.

8. The method of claim 5, wherein the shaping step comprises the step of providing a collimator between a source of the therapeutic x-ray signal and the patient, wherein the collimator is physically arranged to limit the x-ray signal to the target region.

9. The method of claim 5, wherein the target region is determined by irradiating at least a portion of the patient with a diagnostic x-ray signal.

* * * * *